(12) United States Patent
Russo et al.

(10) Patent No.: US 11,564,897 B2
(45) Date of Patent: Jan. 31, 2023

(54) METHOD FOR PRODUCING A POLYPHENOLIC COMPOSITION FROM BARLEY MALT

(71) Applicants: ALIOPHARM S.R.L., Milan (IT); Consiglio Nazionale delle Ricerche, Rome (IT)

(72) Inventors: Gian Luigi Russo, Avellino (IT); Fabrizio Tarricone, Milan (IT); Idolo Tedesco, Avellino (IT)

(73) Assignees: ALIOPHARM S.R.L., Milan (IT); Consiglio Nazionale delle Ricerche, Rome (IT)

( * ) Notice: Subject to any disclaimer, the term of this patent is extended or adjusted under 35 U.S.C. 154(b) by 75 days.

(21) Appl. No.: 16/641,888

(22) PCT Filed: Aug. 20, 2018

(86) PCT No.: PCT/IB2018/056283
§ 371 (c)(1),
(2) Date: Feb. 25, 2020

(87) PCT Pub. No.: WO2019/038658
PCT Pub. Date: Feb. 28, 2019

(65) Prior Publication Data
US 2020/0197342 A1 Jun. 25, 2020

(30) Foreign Application Priority Data
Aug. 25, 2017 (IT) .................. 102017000096298

(51) Int. Cl.
*C12C 7/04* (2006.01)
*C12H 1/22* (2006.01)
(Continued)

(52) U.S. Cl.
CPC .............. *A61K 31/192* (2013.01); *A23L 2/39* (2013.01); *A23L 2/52* (2013.01); *A61K 31/353* (2013.01);
(Continued)

(58) Field of Classification Search
None
See application file for complete search history.

(56) References Cited

U.S. PATENT DOCUMENTS

2007/0254063 A1* 11/2007 Aerts ................. C12C 3/08
426/11
2015/0313271 A1 11/2015 Takeshi et al.

FOREIGN PATENT DOCUMENTS

DE 10256166 A1 6/2006
WO 2005123897 A1 12/2005
(Continued)

OTHER PUBLICATIONS

Montanari et al., "Organic and Phenolic Acids in Beer" Lebensm-Wiss u-Technol vol. 32 pp. 535-539 (Year: 1999).*
(Continued)

*Primary Examiner* — Eric Olson
(74) *Attorney, Agent, or Firm* — Stinson LLP

(57) ABSTRACT

Method for the production of a polyphenolic composition from barley malt, including the fundamental steps of: grinding of the malt grains and splitting into two portions, 20% and 80%; mixing each of the two portions with water to obtain an A mixture and a B mixture, the A mixture being prepared with the 20% portion to obtain a mixture of the malt in water at a final concentration between 9.5% and 20%, the B mixture being prepared with the 80% portion to obtain a mixture of the malt in water at a final concentration between 33% and 60%; thermal cycle; separation of the liquid component from the solid component; boiling of the
(Continued)

liquid component and the addition of hops; rapid cooling of the wort; storage; in which said thermal cycle consists of a first phase and a second phase, in which the first phase applies to the 20% portion (Mixture A) and the second phase during which Mixture B is added to Mixture A. The relative polyphenolic composition obtained according to this method is characterized by the fact that it can be in liquid, powder, dry, and lyophilized form, its use and relative beverage or beer according to the present method not obtained with fermentation methods.

11 Claims, 5 Drawing Sheets

(51) Int. Cl.

| | |
|---|---|
| C12C 1/18 | (2006.01) |
| C12C 5/02 | (2006.01) |
| C12C 1/16 | (2006.01) |
| A61K 31/192 | (2006.01) |
| A23L 2/39 | (2006.01) |
| A23L 2/52 | (2006.01) |
| A61K 31/353 | (2006.01) |
| A61K 31/7034 | (2006.01) |
| C12C 7/20 | (2006.01) |
| C12C 12/04 | (2006.01) |

(52) U.S. Cl.
CPC ............ *A61K 31/7034* (2013.01); *C12C 1/16* (2013.01); *C12C 1/18* (2013.01); *C12C 5/02* (2013.01); *C12C 7/04* (2013.01); *C12C 7/042* (2013.01); *C12C 7/205* (2013.01); *C12C 12/04* (2013.01); *C12H 1/22* (2013.01); *A23V 2002/00* (2013.01)

(56) References Cited

FOREIGN PATENT DOCUMENTS

| WO | 2007016578 A2 | 2/2007 |
| WO | 2014016409 A1 | 1/2014 |

OTHER PUBLICATIONS

Taylor et al., "Mashing with Malted Grain Sorghum" Journal of the American Society of Brewing Chemists vol. 50 issue 1 pp. 13-18 https://doi.org/10.1094/ASBCJ-50-0013 (Year: 1992).*

Igyor et al., "Effect of malting temperature and mashing methods on sorghum wort composition and beer flavour" Process Biochemistry vol. 36 pp. 1039-1044 (Year: 2001).*

Lyumugabe et al., "Characteristics of African traditional beers brewed with sorghum malt: a review" Biotechnol. Agron. Soc. Environ. vol. 16 No. 4 pp. 509-530 (Year: 2012).*

Tippmann et al., "Procedural Investigations of the Lautering Process" Chemical Engineering and Technology vol. 33 No. 8 pp. 1297-1302 DOI: 10.1002/ceat.201000109 (Year: 2010).*

Owuama et al., "Studies on mashing methods for brewing with sorghum" MIRCEN Journal vol. 3 pp. 243-253 (Year: 1987).*

Stephenson et al., "Laboratory-Scale Studies of the Impact of Oxygen on Mashing" J Inst Brew vol. 109 No. 3 pp. 273-283 (Year: 2003).*

Andersen "Modification of the Levels of Polyphenols in Wort and Beer by Addition of Hexamethylenetetramine or Sulfite during Mashing" J Agric Food Chem vol. 49 pp. 5232-5237 DOI 10.1021/jf0105945 (Year: 2001).*

Gerhauser, C., "Beer Constituents as Potential Cancer Chemopreventive Agents," 2005, Eur J Cancer 41/13:1941-1954, 14 pages.

Diller, R.A., et al., "Ability of Prenylflavanones Present in Hops to Induce Apoptosis in a Human Burkitt Lymphoma Cell Line," 2007, Planta Med, 73/8:755-761, XP018022555, Abstract Only.

Ghiselli, A., et al., "Beer Increases Plasma Antioxidant Capacity in Humans," 2000, J Nutr Biochem, 11/2:76-80, Abstract Only, 1 page.

Kondo, K., "Beer and Health: Preventive Effects of Beer Components on Lifestyle-Related Diseases," 2004, Biofactors, 22/1-4: 303-310, Abstract Only, 1 page.

Lust, S., et al., "Xanthohumol Kills B-Chronic Lymphocytic Leukemia Cells by an Apoptotic Mechanism," 2005, MolNutr Food Res, 49/9:844-850, Abstract only, 2 pages.

Miranda, C.L., et al., "Antiproliferative and Cytotoxic Effects of Prenylated Flavonoids from Hops (*Humulus lupulus*) in Human Cancer Cell Lines," 1999, Food Chem Toxicol, 37/4:271-285, Abstract Only, 1 page.

Melson, R.L., et al., "Neither Dietary Ethanol nor Beer Augments Experimental Colon Carcinogenesis in Rats," 1985, Dis Colon Rectum, 28/6:460-462, Abstract Only, 1 page.

Rivero, D., et al., "Inhibition of Induced DNA Oxidative Damage by Beers: Correlation with the Content of Polyphenols and Melanoidins," 2005, J Agric Food Chem, 53/9:3637-3642, Abstract Only, 1 page.

Tedesco, I., et al., "Antioxidant and Cytotoxic Properties of lyophilized Beer Extracts on HL-60 Cell Line," 2005, Nutr Dancer, 52/1:74-83, 10 pages.

Visioli, F., et al., "Polyphenols and Human Health: A Prospectus," 2011, Critical Reviews in Food Science and Nutrition, 51/6:524-546, Abstract Only, 1 page.

Del Rio, D., et al., "Dietary (Poly)phenolics in Human Health: Structures, Bioavailability, and Evidence of Protective Effects Against Chronic Diseases," 2013, Antioxid Redox Signal, 18/14:1818-1892, 75 pages.

International Search Report issued in PCT/IB2018/056283, dated Oct. 23, 2018, 4 pages.

Written Opinion issued in PCT/IB2018/056283, dated Oct. 23, 2018, 6 pages.

* cited by examiner

METHOD FOR PRODUCING A POLYPHENOLIC COMPOSITION FROM BARLEY MALT

REFERENCE TO RELATED APPLICATIONS

The present application is the 371 National Stage Application of International Patent Application Serial No. PCT/IB2018/056283, filed Aug. 20, 2018, which claims the benefit of Italian Patent Application No. 102017000096298, filed Aug. 25, 2017, the entire contents of which are incorporated herein by reference.

This invention refers in general to the food, nutraceutical, and pharmaceutical sectors applied to cereal by-products, more specifically to a polyphenolic composition obtained from cereals. In detail, this invention refers to a method for producing a polyphenolic composition from malt and hops; the abovementioned polyphenolic composition has evident healthy effects. More specifically, this polyphenolic composition obtained from malt and hops is characterized by a high content of natural polyphenols, demonstrating significant anti-oxidant and anti-tumor effects.

The healthy effects of some alcoholic beverages like wine and beer are known, if consumed in moderate amounts; some studies have demonstrated the correlation between the consumption of beer and the prevention of heart diseases, cancer, and osteoporosis (Gerhauser 2005; Kondo 2004, Rivero et al. 2005), as well as the correlation between beer consumption and the anti-oxidant power of the serum (Ghiselli et al. 2000). The positive association between moderate consumption of alcoholic beverages and low risk of degenerative diseases was also linked to the polyphenol content.

As is known, phenolic substances are a class of natural organic compounds characterized by the presence of at least one aromatic ring, mono- or multi-substituted by hydroxyl groups. Among these, flavonoids have a base structure with two aromatic rings linked by a heterocyclic compound through either a hydroxylated, glycosylated, or methylated connection. The most common vegetable flavonoids are the flavans, which are more commonly present in beer, (+) catechin, (−) epicatechin, gallocatechin, and epigallocatechin, in a monomer, dimer, trimer, or polymer form.

Phenolic compounds as donors of hydrogen possess an anti-oxidant quality linked in hydroxyl groups linked to aromatic structures and to the geometry of the molecule; also the degree of polymerization influences the anti-oxidant action.

In particular, it was seen that the anti-oxidant action of beer is correlated to the total polyphenol content (Rivero et al., 2005; Tedesco et al., 2005) and that beers normally have a total polyphenol content of approximately 489 mg/l, or double that of a light nonalcoholic beer. It is also known that about 20-30% of the polyphenols in beer derive from hops, while 70-80% derive from malt (Benitez et al., 1997).

Indeed, recent studies have focused on the interesting biological properties of compounds deriving from hops and found in beer, like xanthohumol, isoxanthohumol and bitter acids. These molecules seem to be able to perform an anti-tumor action in both cellular and animal models. In particular, the xanthohumol acts as an anti-tumor agent both in vitro and in ex vivo models of chronic lymphocytic leukemia (Lust et al., 2005; Miranda et al., 1999).

Several works were known to be state-of-the-art concerning the chemo-preventive effectiveness of beer in experimental carcinogenesis models; for example, Nelson & Salmeson (1985) demonstrated that the chronic consumption of beer reduced the formation of gastrointestinal tumors induced by dimethylthirizine in rats.

On the other hand, Tedesco et al. (2005) verified the high probability that the synergic effect of phenolic compounds in beer triggers the inhibition of the proliferation of tumor cells and the induction of apoptosis. Indeed, the anti-proliferative activity of individual molecules added to the tumor cells, at an average concentration found in commercial beers used, was absent in tests where the biological activity of the lyophilizate in toto was measured.

With reference to the health properties of some alcoholic and non-alcoholic beverages made with cereals, various patent documents concerning technical status are also known.

The patent document US20080261897 describes a formulation containing epigallocatechin to reduce bitterness; in the patent in question, there is no reference to a specific polyphenol composition and the method used to obtain the beverage; lastly, there is no reference to the biological activity of said composition.

Patent US2005266120 describes a method for the production of a fermented beverage similar to beer and non-alcoholic, fermented using a slow fermentation process; this beverage contains a very low quantity of alcohol—0.5% (p/v)—obtained by the fermentation of fungi of the genre *Monascus*; these fungi ferment alcohol slowly and have a high anti-oxidant activity to control the fermentation of the alcohol.

The patent document US20080213433 describes a non-alcoholic beverage with a polyphenol base, making particular reference to the trans-resveratrol in a concentration between 5-300 mg/kg. This document also contains a description of a method that provides for the addition of this polyphenol composition to a variety of beverages, including coffee and other barley products.

The need to create a polyphenolic composition to add to the beverages marketed, or directly produced in beverage form, derives from the fact that normal cooking processes, like in the production of beer, or toasting, like in the production of coffee, cause a depletion of the polyphenol content naturally found in the original foodstuff. This invention describes an all-natural method for preserving the high quantity of natural polyphenols present in barley malt to obtain a characteristic polyphenol composition. Moreover, it has been noticed, in the technical sector of reference, the need to provide a beverage that has a high content of polyphenol naturally present in the foods, but that is a totally non-alcoholic product (0% alcohol content); said beverage is different from a non-alcoholic beer in that by Italian law the denomination 'non-alcoholic' beer is reserved for products with Plato degrees no less than 3 and no higher than 8 and with an alcoholic strength by volume no higher than 1.2%. The denomination 'light beer' is reserved for the product with a Plato degree no less than 5 and no higher than 10.5 and with an alcoholic strength by volume between 1.2% and 3.5%. The denomination "beer" is reserved for the product with a Plato degree higher than 10.5 and with an alcoholic strength by volume higher than 3.5%.

In the light of the above, the scope of the present invention is therefore to provide a natural polyphenolic composition starting from malt and hops that preserves most of the polyphenols present in the raw materials intact, thereby obtaining a composition characterized by high anti-oxidant and anti-tumor activities. It is also scope of the present invention to provide a method for producing the abovementioned polyphenolic composition that preserves the largest possible quantity of polyphenols present in the malt, thereby obtaining a composition characterized by high antioxidant and anti-tumor activities. Said method does not provide for the use of the fermentation phase.

Yet another scope of this invention is to provide a polyphenolic composition starting from unfermented malt and hops in the form of a completely non-alcoholic functional beverage, containing 0% alcohol, naturally rich in polyphenols and not artificially enriched with polyphenols.

Said beverage obtained from unfermented malt, naturally rich in polyphenols, is completely non-alcoholic. As it is a beverage with no alcohol, 0% alcohol content, it can be used by any type of user: children, the elderly, or people with specific pathologies for which the consumption of polyphenolic compositions is suggested but the consumption of alcoholic beverages is not recommended, even if in moderate quantities.

This invention therefore provides a method for the production of a polyphenolic composition starting from unfermented malt.

In a preferred embodiment, this invention provides a polyphenolic composition starting from unfermented malt comprising polyphenols such as: caffeic acid, m-Coumaric acid, p-hydroxybenzoic acid, sinapinic acid, epicatechin, protocatechuic acid, catechin, p-Coumaric acid, ferulic acid, vanillic acid, chlorogenic acid and their mixtures, and characterized in that it contains chlorogenic acid. Other aspects of this invention, including the forms of realization, medical uses, anti-oxidant and anti-tumor health benefits are described in the following claims attached.

The aforementioned claims are understood to have been included herein. This invention will become more evident from the detailed description that follows, with reference to the drawings attached that illustrate an embodiment of the polyphenolic composition starting from unfermented malt and hops and the relative production method, where:

It is provided, in the following, the description of an exemplary embodiment, as such not restricted, of the production method of the polyphenolic composition starting from unfermented malt and hops and the relative composition obtained.

DESCRIPTION OF THE INVENTION

In the following all the % indicated are % in weight.

The production method of the above-mentioned polyphenolic composition provides the use, by way of example, of the following raw materials mixed with water: light and dark barley malt in varying proportions depending on the color desired for the final product, the larger the proportion of dark malt (more toasted) the more intense the color of the finished product; hops; acidifiers, those usually used in this field, preferably citric acid, lactic acid, and orthophosphoric acid, useful for bringing the pH of the final mixture within the interval of 4.0-4.6, preferably 4.2.

Figure 1:
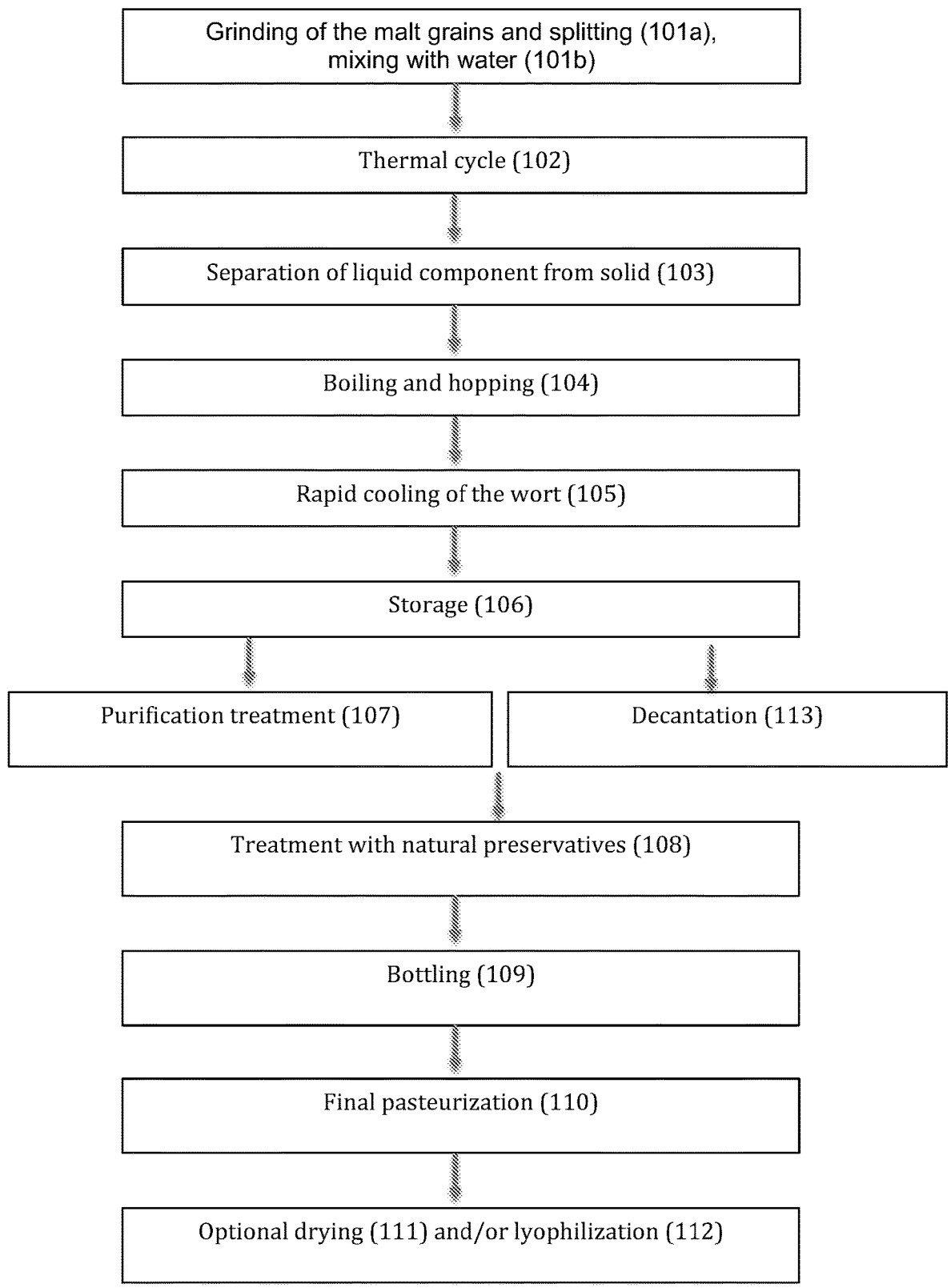
FIG. 1 is the block diagram of the production method of the polyphenolic composition obtained from unfermented malt and hops.

With reference to FIG. 1, the method for the production of the above-mentioned polyphenolic composition comprising the following steps:

1. grinding of malt grains and splitting in two portions, 20% and 80%, 101*a*;
2. mixing 101*b* each of the two portions with water to obtain a mixture A and a mixture B. The A mixture is prepared with the 20% portion to obtain a mixture of malt in water with a final concentration between 9.5% and 20%. Mixture B is prepared with the 80% portion to obtain a mixture of malt in water with a final concentration between 33% and 60%. An example of production requires that the A mixture be obtained with 360 kg of ground malt in 28±10 hl of water, and that the B mixture be obtained with 1470 kg of ground malt in 35±10 hl of water.
3. thermal cycle 102 with two consecutively phases, as indicated below;
4. separation of the liquid component from the solid component (the spent grains) 103 at the final temperature reached in the thermal cycle (76±5° C.) and subsequent washing of the spent grains at the same temperature (76±5° C.);
5. boiling of the liquid component resulting from step 4 and addition of hops 104 (thereby obtaining the beer wort);
6. rapid cooling of the wort 105 at a rate of 1.85±0.8° C. per minute;
7. storage at a final temperature after cooling 106 without additional yeasts;
8. optional purification treatment 107;
9. optional treatment with natural preservatives 108;
10. optional bottling 109;
11. optional thermal treatment to prolong preservation, actually a pasteurization 110;
12. optional drying 111 with known techniques, for example lyophilization 112.

More specifically, the production method for the polyphenolic composition from unfermented malt is characterized by a thermal cycle (step 3) which makes it possible to preserve the largest quantity of polyphenols naturally present in the malt, immediately after its grinding.

This thermal cycle consists of a first phase and a second phase.

The first phase of this thermal cycle is applied only to the 20% of the malt mixture (mixture A), and the second phase is applied to the entire batch, or the 20% previously treated to which the remaining 80% (mixture B) has been added.

The first phase of the thermal cycle is characterized by a heating process when an initial gelatinization of the starch takes place. The heating in conducted for a period of 1-2 minutes, preferably 1 minute, until it reaches a temperature of 71° C., preferably 66±5° C., or more preferably 66° C. This heating phase is followed by a holding pause of temperature maintenance for 20-30 minutes, preferably 20 minutes, followed by an increase in the temperature for about 10-20 minutes, preferably 15-16 minutes, until the mixture boils (typically at 100° C.).

Following the heating, a pause in the boiling is required for 10-25 minutes, followed by cooling phase lasting 10-18 minutes, preferably 12±2 minutes, more preferably 14 minutes, until the mixture reaches a temperature between 45° C. and 55° C.

The second phase of the thermal cycle is applied to all the mixture, which means that the remaining portion (mixture B) is added, after being heated to the same temperature reached by mixture A, or between 45-55° C., preferably 50° C. The temperature between 45-55° C. is maintained for 15-30 minutes and constitutes the pause proteolytic phase during which the protease enzyme breaks up the proteins into polypeptide fractions. Then mixture undergoes successive heating in three stages with temperatures increasing between 60° C. and 80° C. The first stage of heating to 63±2° C. is reached in 7-11 minutes and maintained for about 37-42 minutes.

The second heating stage at 72±5° C. is reached in 4-10 minutes and maintained for about 37-42 minutes;

The third heating stage at 76±2° C. is reached in 3-10 minutes and maintained for about 100-300 minutes.

The first two stages of heating constitute the saccharification stages that make it possible for the beta-amylase and alpha-amylase enzymes to break up the starches.

The final stage of heating is followed by the pouring of the mixture into a filtering vat. Later, at the same temperature as the said thermal cycle, comes the separation, for example for filtration and/or decanting, of the dregs (essentially the spent grains) from the liquid component (the wort) Once separated, the dregs are washed with water and the washing water is added to the wort. It is preferable to carry out at least three washes of the spent grains.

The wort, maintained at the temperature of the third heating stage, is collected in a storage container (optional phase for the cooking room management needs, and can be omitted) and transferred to a heater where the hops are added in a quantity of up to 0.5%, preferably 0.2%-0.3%. By way of example, for a quantity of malt of 1830 kg, 4 kg of hops extract and 1.5 kg of spalt hops can be used (these quantities may vary in relation to the alpha acids content). This wort with the hops added then undergoes a further heating and boiling phase lasting between 40-100 minutes, typically at 108° C. for about 60 minutes. In a normal beer production process, the hops are added to make the beer more bitter, thanks to the component of the alpha acids, and aromatic, thanks to the beta acids and essential oils. Successively, steam is preferably added to the wort at a temperature >100° C., from the bottom up to eliminate unpleasant volatile compounds. The boiling phase of the wort with the hops added is followed by a cooling until a temperature between 2-10° C., preferably 2-4° C., is reached.

After cooling, wort is sent into storage and aging tanks for at least 3 days. After cooling the wort is sent to a storage tank and aged for at least 3 days. This aging process may be prolonged for several months. This step does not call for any yeasts to be added, contrary to the beer production process where yeasts are added at this step. Not adding these yeasts influences the polyphenolic composition and the obtaining of a product with a 0% alcohol content; it is indeed known that yeasts normally use fermentable sugars to obtain alcohol and carbon dioxide.

Once the aging step has ended, there is another optional step, the elimination of impurities 107; this step 107 may take place through a simple decanting or by means of filtering with Diatomaceous earth to obtain the final beverage. Step 108, which is optional, will be a treatment of the beverage with natural preservatives; in a preferred embodiment, these preservatives would be coloring malt and ascorbic acid.

Other optional steps of bottling and pasteurization may follow; or even drying and/or lyophilization with known technical procedures.

The polyphenolic composition obtained with the method provided with this invention is characterized by the following ratios between the main phenolic components:

TABLE 1

Polyphenolic composition obtained with the method provided with this invention

| Main phenolic compounds of the polyphenolic composition | Ratio ranges relative to the phenolic compositions (Caffeic Acid molecule concentration is set as equal to 1) |
|---|---|
| Caffeic Acid | 1 |
| Chlorogenic Acid | 0.83-1.01 |
| m-Coumaric Acid | 1.04-1.27 |
| P-hydroxybenzoic Acid | 1.13-1.39 |
| Sinapinic acid | 1.33-1.63 |
| Epicatechin | 1.67-2.04 |
| Protocatechuic Acid | 1.73-2.11 |
| Catechin | 2.39-2.93 |
| p-Coumaric Acid | 5.13-6.27 |
| Ferulic Acid | 8.46-10.3 |
| Vanillic acid | 2.47-3.01 |

The method provided by this invention differs from standard methods of beer production for the fact that, while in a beer production process the polyphenolic content tends to be reduced due to the cloudiness and the flavor granted by some polyphenols, in the method provided in the invention each passage was modified in order to preserve the polyphenolic content of the malt, thereby obtaining an original polyphenolic composition that, in its liquid form, is different from those commonly known to be contained in beers. The abovementioned method does not need yeasts to be added and therefore fermentation is not induced, making it possible to obtain a beverage from malt and hops that contains 0% alcohol and preserves a high polyphenol content, as well as obtain the polyphenolic composition as illustrated in Table 1. The polyphenolic composition from unfermented malt and hops that this invention provides is characterised by the fact that it can be in either liquid or powdered form (dried or lyophilized). Said composition can be used as a food or beverage, as a functional food, as dietary supplement, or as a pharmaceutical in typical pharmaceutical forms like, by way of example and not limited to:

solid pharmaceutical forms (tablets, pills, hard capsules, powders, granules, suppositories)

semi-solid pharmaceutical forms (gels, ointments, lubricants, pastes)

liquid pharmaceutical forms (syrups, vials, drops, eye drops).

Another embodiment of the polyphenolic composition from unfermented malt and hops provided by this invention is related to its use in a generic non-alcoholic beverage that, by way of example but my no means exhaustive, belongs to the group that comprises fruit juices, milk, soy-based beverages, rise-based beverages, energy drinks, etc.

Yet another embodiment of the polyphenolic composition obtained from unfermented malt and hops provided by this invention is related to its use in dietary supplements and/or a generic foodstuff.

The relative quantity ratios in Table 1 are also important in the light of the 'synergistic' type biological activity that can be attributed to the polyphenols that make up the polyphenolic composition provided by this invention and its embodiment as a functional beverage.

The polyphenolic profile of the functional beverage in question is characteristic and original above all if compared to that of non-alcoholic beers.

The functional beverage has an intermediate profile between a dark and a light beer and this profile is characterized by the presence of chlorogenic acid. Chlorogenic acid, an ester of caffeic acid, rarely present in the list of phenolic compositions identified in the most common types of beer (light beer, dark beer, and non-alcoholic beer) instead appears to be present and in measurable quantities in the list of polyphenols of the functional beverage. Chlorogenic acid is known for its anti-oxidant power. The characteristic presence of chlorogenic acid in the polyphenolic composition obtained from malt and hops, can represent a specific marker of this composition. The pharmaceutical indications of the composition are the following: treatment of chronic and degenerative pathologies (cardiovascular, neuro-degenerative, autoimmune, metabolic disorders and tumors). In the literature are known publications where the use of polyphenolic compositions is described as an aid in treating chronic and degenerative pathologies, like: Francesco Visioli et al. (2011) and Daniele del Rio et al. (2013).

The polyphenolic composition according to the invention can be administered as a food, as a dietary supplement, or as a pharmaceutical to animal and elderly, adult, adolescent, children, and infant.

In a particular embodiment, the polyphenolic composition, according to the present invention, is provided in liquid form, as a functional non-alcoholic beverage, using the method explained above or as a powder to be dissolved in a liquid, like water or milk or fruit juice. The total quantity of natural polyphenols in the above-mentioned polyphenolic composition in liquid form as a functional beverage, or as a non-alcoholic beer, is greater than 250 mg/l.

The following examples can be considered, by way of example and not of limitation, of this invention.

EXAMPLE 1

By way of example, for the production of 100 hl nominal of the above-mentioned beverage, characterized by a final value of 12.87 Plato Degrees, below are the quantities of raw materials: 1.8 kg of Pilsen barley malt; 10 kg of toasted "dark" roasted barley malt; 4.0 kg of Hops extract at 30%; 1.8 kg of Hops pellets 4.6%; 2.8 kg of Calcium Sulphate and 1.8 kg of phosphoric acid at 75%.

According to the method provided in this invention, the thermal cycle 102 provides the processing of the A and B mixtures of malt and water (containing respectively 20% and 80% of the malt) at different temperatures and times according to the following table, where the process parameters are indicated:

| Process details | Temperature (° C.) | Time (min) |
| --- | --- | --- |
| Infusion of the 20% malt mixture | 60 | 17 |
| Heating | 66 | 1 |
| Pause | 66 | 20 |
| Heating | 100 | 16 |
| Boiling | 100 | 15 |
| Pause | 100 | 5 |
| Cooling | 50 | 14 |
| Addition of the 80% malt mixture | 50 | 15 |
| Pause | 50 | 20 |

-continued

| Process details | Temperature (° C.) | Time (min) |
| --- | --- | --- |
| Heating | 63 | 9 |
| Pause | 63 | 40 |
| Heating | 72 | 6 |
| Pause | 72 | 40 |
| Heating | 76 | 5 |
| Pouring into the filtration tank | | 11 |

The filtration step 103 takes place during the preparation of the wort in the "cooking room" with the aim to remove the spent grains from the wort. This takes place in the filtration tank by the force of gravity; said filtration consists of a filtration of the wort and is carried out for the purpose of separating the solid component (spent grains) from the liquid component (beer wort). In particular, the separated spent grains are washed three times for the purpose of extracting more nutritional substances from the spent grains themselves.

| Process details | Temperature (° C.) | Time (min) | Quantity (hl) |
| --- | --- | --- | --- |
| Pause for 5 minutes in the filtration tank | 76 | 5 | 90 |
| Cloudy wort | 76 | 7 | |
| First wort | 76 | 84 | 53 |
| First washing | 76 | 20 | 15 |
| Second washing | 76 | 25 | 15 |
| Third washing | 76 | 15 | 10 |

The boiling and hopping step 104 provides the boiling of the filtered wort and hopping. This process consists of the filtered wort being collected in a storage tank called "5$^{th}$ heater". Once the 5$^{th}$ heater is full, and so at the end of the wort filtration, the wort is sent in the Whirlpool where the successive heating and boiling phases will take place. The adding of the hops (4.0 kg of hops extract at 30%, 1.8 kg of Hops pellets 4.6%) takes place when the Whirlpool is full, so when all the filtered wort has been poured from the 5$^{th}$ heater to the Whirlpool and heating can begin.

| Process details | Temperature (° C.) | Time (min) | Quantity (hl) |
| --- | --- | --- | --- |
| 5$^{th}$ heater full (collection of the filtered wort from the beginning of the first wort phase to the end or the third washing) | 76 | 144 | 99 |
| Whirlpool full (pouring from 5$^{th}$ heater to the Whirlpool) | 76 | 20 | 99 |
| Heating | from 76 to 108 | 55 | 99 |
| Boiling + pause | 108 | 60 | 93 |
| Stripper + cooling | from 99 to 2 | 53 | 93 |

The phase denominated "stripper" consists of the injection of steam into the wort, from below upwards, before the cooling, in order to remove unpleasant volatile compounds released with the boiling.

The wort cooling step 105 calls for the cooling of the wort until it reaches a temperature of 2° C. to send it into the aging tank and hence start the storing stage 106. Cooling is obtained through a plate heat exchanger with cold water cross-flow.

The storage step 106 consists of the transfer of the wort into an aging tank for a storage time of about 3 days, without the addition of yeasts, contrary to what occurs during the beer production process where yeasts are added during this stage.

The filtration phase 107 consists of the use of Diatomaceous earth to remove the impurities from the aged beverage, thereby clarifying it. The filtration phase 107 takes place in a room called the "filtration room" using a horizontal pressure filter with cardboard filtering layers and using Diatomaceous earth as a technological adjuvant. Generally, the sequestrants used during this phase also reduce the polyphenol content. Some beer producers use sequestrants to deliberately reduce or eliminate the polyphenol content, as these compounds generate cloudiness.

In a further development of the invention, the filtration phase 107 is replaced by a decantation phase 113, which consists of the removal of impurities from the aged beverage by collecting the upper part with no impurities; the replacement of the filtration phase 107 with a decantation phase 113 results in a further increase of polyphenols in the polyphenolic composition.

The treatment phase 108 consists of adding coloring malt extract and ascorbic acid. The coloring malt extract is added to mask the cloudiness and reduce the degree of the polyphenols to a minimum, thereby boosting the functional capacity of the functional beverage.

It follows the bottling 109 and final pasteurization 110 phases. Further passages of this method may include drying 111 or lyophilization 112. In a preferred realization the drying process 111 include also the 50° C. treatment.

The total quantity of polyphenols in the polyphenolic composition in liquid form as a functional beverage is about 300 mg/l, which is comparable to the quantity of polyphenols in a typical light beer (>250 mg/l) and almost double that of non-alcoholic beers on the market.

TABLE 2 comparison of total polyphenol concentrations

| Type of beer | Polyphenols (mg/l)[1] | Polyphenols (mg/l)[2] |
| --- | --- | --- |
| Functional Beverage | 300 | — |
| Light Beer | 303 | 280 |
| Dark Beer | 533 | 420 |
| Non-alcoholic Beer | — | 122 |

[1]The data collected concerning the polyphenolic composition of the functional beverage were obtained at CNR laboratories.
[2]The data collected concerning the polyphenolic composition of the different beers were obtained from the Phenol-Explorer data bank (http://phenol-explorer.eu/), which are the averages calculated using measurements taken by various authors.

The polyphenolic composition in liquid form as a functional beverage shows a characteristic polyphenolic profile that stands, more or less, in an intermediate level between the polyphenolic profile of light beers and the polyphenolic profile of dark beers, and is also obviously different from the polyphenolic profile of non-alcoholic beers. The polyphenolic composition of the functional beverage provided with this invention is characteristic and new compared to standard polyphenolic compositions of beers in that it contains measurable quantities of chlorogenic acid, generally not reported in the literature as a component of the polyphenolic compositions of beers.

By way of example, Table 3 illustrates the polyphenolic profile of the polyphenolic composition in functional beverage form obtained with the method described according to this invention, with the detail of the relative ratios between the polyphenolic molecules present.

TABLE 3 polyphenolic profile of the polyphenolic composition in functional beverage form

| Main phenolic compounds of the polyphenolic composition | Relative ratios of the phenolic compositions (Caffeic Acid molecule concentration is set as equal to 1) |
| --- | --- |
| Caffeic Acid | 1 |
| Chlorogenic Acid | 0.92 |
| m-Coumaric Acid | 1.15 |
| p-Hydroxybenzoic Acid | 1.26 |
| Sinapinic Acid | 1.48 |
| Epicatechin | 1.85 |
| Protocatechuic Acid | 1.92 |
| Catechin | 2.66 |
| p-Coumaric Acid | 5.70 |
| Ferulic Acid | 9.40 |
| Vanillic acid | 2.74 |

[1]The data collected concerning the polyphenolic composition of the functional beverage were obtained at CNR laboratories.

TABLE 4

Comparison of functional beverage polyphenolic profile vs. dark beer, light beer, and non-alcoholic beer.

| Phenolic compound | Functional beverage[1] | Dark beer[2] | Light beer[2] | Non-alcoholic beer[2] |
| --- | --- | --- | --- | --- |
| Caffeic Acid | 1 | 1 | 1 | 1 |
| Chlorogenic Acid | 0.92 | 0 | 0 | 0 |
| m-Coumaric Acid | 1.15 | 0 | 0.66 | 0 |
| p-Hydroxybenzoic Acid | 1.26 | 2.33 | 32 | 0.73 |
| Sinapinic Acid | 1.48 | 1 | 0.66 | 0.73 |
| Epicatechin | 1.85 | 0.33 | 2 | 0.55 |
| Protocatechuic Acid | 1.92 | 1.33 | 1.66 | 27 |
| Catechin | 2.66 | 0.67 | 3.66 | 10 |
| p-Coumaric Acid | 5.70 | 1.67 | 3.33 | 4 |
| Ferulic Acid | 9.40 | 3 | 8.66 | 12 |
| Vanillic acid | 2.74 | 5.67 | 2.33 | 3 |

[1]Experimental data of the polyphenolic composition in functional beverage form obtained from CNR laboratories.
[2]The data collected concerning the polyphenolic composition of the different beers were obtained from the Phenol-Explorer data bank, which are the averages calculated using

EXAMPLE 2

The polyphenolic composition obtained with the method described according to this invention has demonstrated an anti-tumor activity in murine models at a dosage D between 3 and 60 mg/kg, or higher than 3 and lower than 60 mg/kg, or 3<D<60.

In particular, the anti-tumor activity, both in the onset phase of the cancer and in the reduction of existing tumor, is noticeable at doses of 3 mg/kg; with higher doses of 30 mg/kg, the polyphenolic composition acts mostly by preventing the transformation of preneoplastic lesions in tumors.

The anti-oxidant activity is demonstrable at doses of 30 mg/kg; a significant reduction in the peroxides in the serum can be noticed with doses of 100-300 mg/kg.

TABLE 5 correspondence between dosages and volumes of the polyphenolic
composition administered to murine models and humans.

| Concentration of the polyphenolic composition by weight | Concentration of the polyphenolic composition by volume | Mouse | Man |
|---|---|---|---|
| 1 g/kg | 8.5 ml/kg | 0.3 ml | 600 ml |
| 30 mg/kg | 0.25 ml/kg | 0.008 ml | 17.5 ml |
| 3 mg/kg | 0.025 ml/kg | 0.0008 ml | 1.75 ml |

Table 5 illustrates a series of equivalences to calculate the correspondence in volume of polyphenolic composition, administered in beverage form, administered to a man of an average weight of 70 kg to obtain the desired biological effects as observed in mice, which is to say anti-tumor and anti-oxidant actions at indicated doses of 3 and 30 mg/kg. As can be seen in the table above, by extrapolating the data obtained on mice to man, the quantity of the polyphenolic composition, administered in functional beverage form, administered to a subject with an average weight of 70 kg are extremely low; this indicates an extremely active composition at very low doses, as is demonstrated by the experimentations that follow.

The anti-tumor activity was studied in vitro on pre-clinical models (cellular lines and animal models) using the above-mentioned functional composition in lyophilized form and/or dried. The studies conducted highlighted the following effects:

1. Reduction in the vitality of cell lines of various origins; Reduction of the vitality of HL-60 cell lines. These cells were selected in that they were previously used for a screening of the antiproliferative activity of 48 commercial beers (Tedesco et al., 2005). The HL-60 derive from a human acute promyelocytic leukemia and when treated for 24 h with 10% (v/v) of functional beverage, corresponding to about 6 mg of dry weight and about 60 µM equivalent of quercetin, in terms of total polyphenols, demonstrated a reduction in vitality of about 40% (neutral red spot assay). Tedesco et al., 2005, reported that this cytotoxicity is to be attributed, bona fide, to the activation of cellular death by apoptosis. Finally, it is useful to report that in lymphocytes from peripheral blood prepared by normal subjects and used as a "control of normal cells" compared to HL-60, the functional beverage, under the same experimental conditions, induced a cytotoxicity of less than 5%, indicating greater effectiveness against the malign phenotype.

2. Reduction of the formation of aberrant crypts, foci, polyps and tumors induced by the AOM in an experimental model of colorectal tumors in mice, with oral administration of the polyphenolic composition.

The anti-oxidant activity was demonstrated by measuring peroxide concentration (equivalents of $H_2O_2$) in the serum of treated mice; the concentration of peroxides is an index of the oxidative stress status of the organism. The experimentation included the use of the polyphenolic composition in the form of samples concentrated by drying. As illustrated in Table 5, treatment by drying causes a lesser reduction in polyphenols than lyophilization. Moreover, a slight increase in anti-oxidant activity and cytotoxicity of the dried samples was evident.

TABLE 6 content in polyphenols, anti-oxidant activity and cytotoxicity of
the lyophilized and dried samples of polyphenolic composition.

| Polyphenolic composition | Polyphenols (µM EqQ) | Anti-oxidant activity (DPPH %) | Vitality (% Ctrl) |
|---|---|---|---|
| liquid (control) | 887 | 9.2 | 65 |
| Lyophilized | 558 | 7.12 | 65 |
| Dried | 748 | 10.9 | 60 |

In the following is showed experimental details of the tests conducted on polyphenolic composition samples according to this invention.

Experiment 1

The first experiment consisted in the administration of the polyphenolic composition in dried form (hereinafter Db0%) in mice treated with azomethane (AOM); the experimentation lasted 14 weeks.

The treatment with AOM called for the administration of 10 mg/kg via intraperitoneal injection in 4 successive doses over 4 consecutive weeks (one dose every weekend). The dried Db0% was administered orally 5 times per week for each week, beginning with the first week to the fourteenth, following which the mice were sacrificed.

The controls were represented by mice that were inoculated via intraperitoneal injection 5 ml/kg of physiological solution (AOM control) and mice administered spring water (Db0% control).

The dosage used for the test was a range of doses between 3-300 mg/kg.

This dosage was identified by conducting a preliminary acute toxicity test, in which it was found that at doses between 5-10 g/kg, the dried product caused the death of animals; on the other hand, doses between 0.3 and 1 g/kg resulted in a reduction in the body weight of the mice, which became significant at doses of 1 g/kg. The maximum dose used was therefore 300 mg/kg.

Following the treatment with AOM, it was demonstrated that, over a period of 13 weeks, the mice developed both aberrant crypt foci (preneoplastic lesions); in the colon-rectum of the mice there were also noticeable polyps and tumor.

Figure 2A:
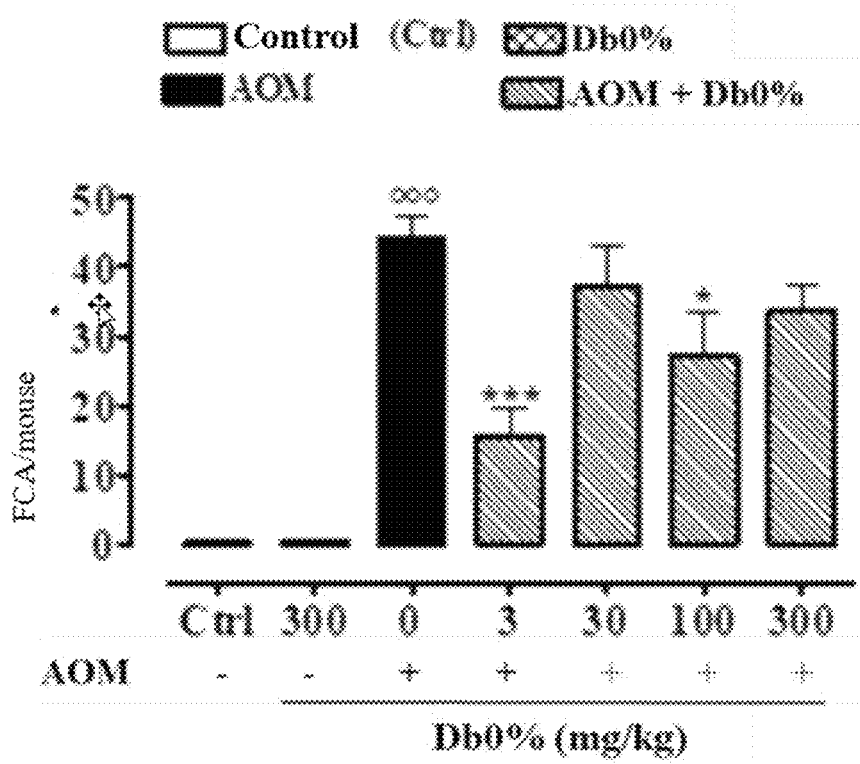
FIG. 2 illustrates the effect of the polyphenolic composition this invention provides on the formation of total ACF (aberrant crypt foci) A (FIG. 2A) and foci constituted by 4 or more aberrant crypts (FIG. 2B) induced in the colons of mice by AOM (azomethane)
Figure 2B:
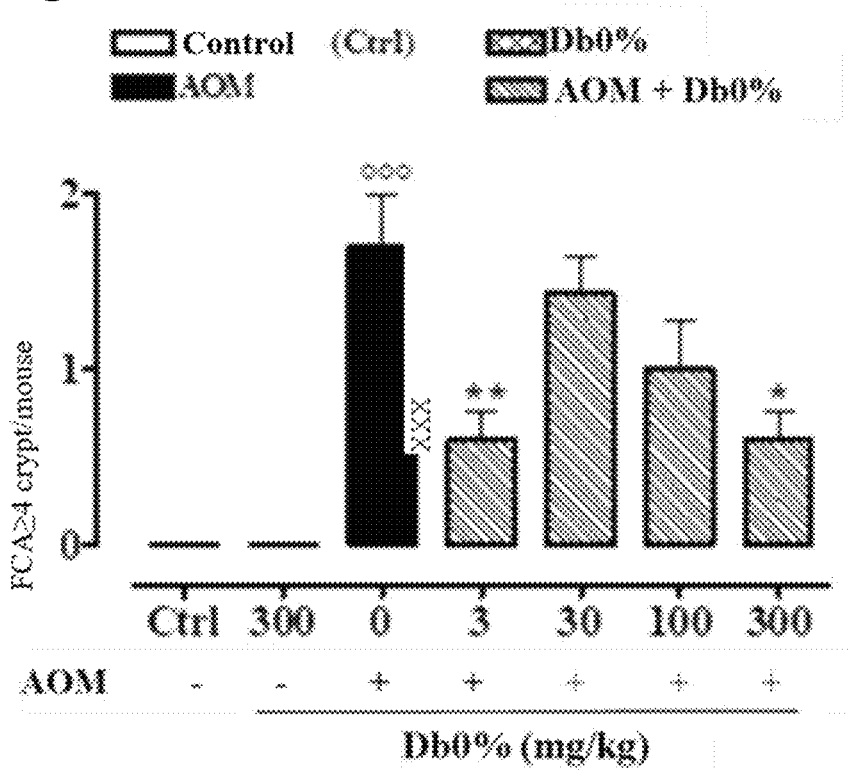

FIGS. 2A and 2B illustrate the effect of administering different concentrations of the dried Db0% (3, 30, 100, 300 mg/kg) on the formation of total aberrant crypt foci (FIG. 2A) and foci consisting of 4 or more aberrant crypts in the colons (FIG. 2B) of the mice treated with AOM.

Figure 3A:
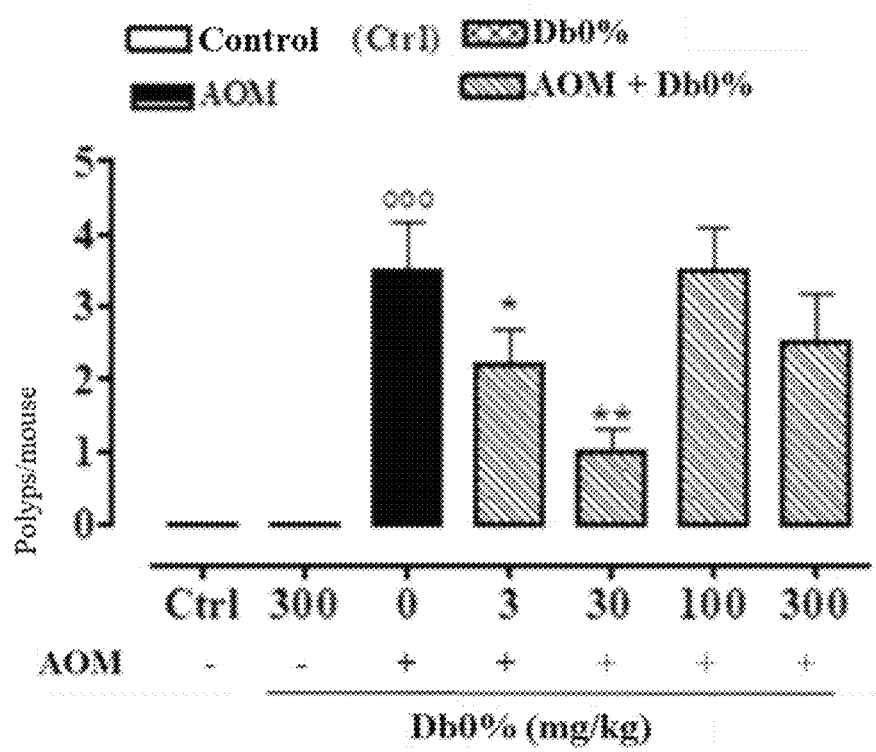
FIG. 3 illustrates the effect of the polyphenolic composition this invention provides on the formation of polyps (FIG. 3A) and tumors (FIG. 3B) induced in the colons of mice by AOM (azomethane)
Figure 3B:
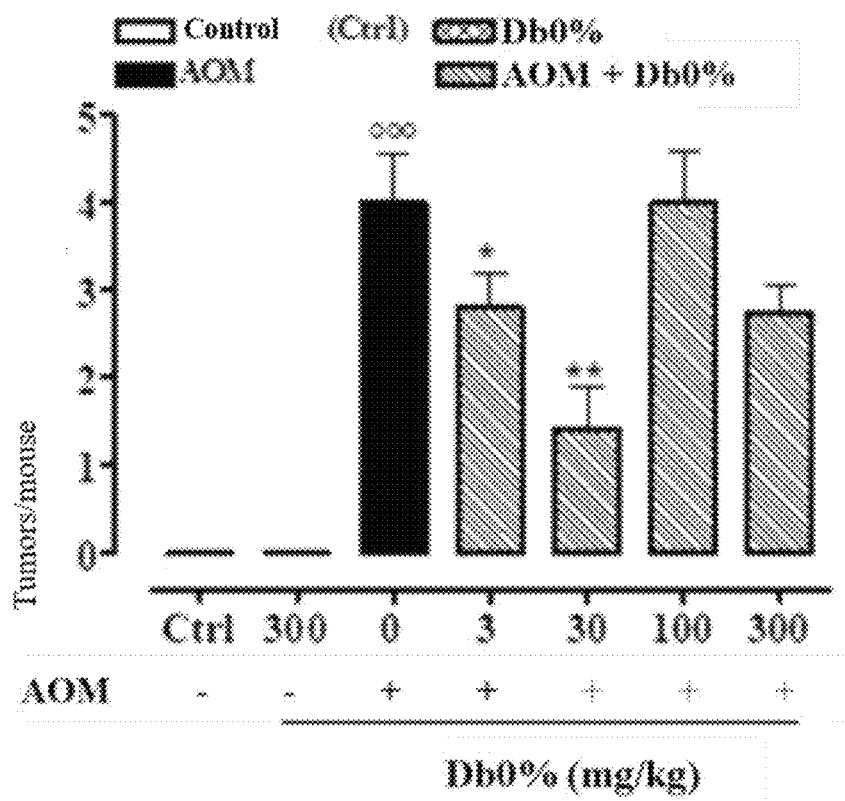

FIG. 3 illustrates the effect of administering different concentrations of the dried Db0% (3-30-100-300 mg/kg) on the formation of polyps (FIG. 3A) and tumors (FIG. 3B) induced in the colons of mice treated with AOM.

The results indicate the anti-tumor activity of the dried Db0% on colorectal disease. In particular, it highlights that the extract of the lowest dosage, or 3 mg/kg act as soon as the first phase of the onset of the tumor, or by reducing the formation of the preneoplastic lesions during the transformation of the preneoplastic lesion in neoplastic lesions (polyps and tumors).

The dosage of 30 mg/kg acts mainly during the second phase or, in other words, by impeding the transformation of preneoplastic lesions in neoplastic lesions (polyps and tumors), especially in comparison to previous dosages.

In general, a lesser efficiency of the dried product at high concentrations was noticed when compared to low concentrations.

This behavior can be observed in many experiments where raw extracts/preparations containing bioactive molecules of different natures are used and can be the result of the combination of various events that occur simultaneously (synergistic effect).

Some of these events may depend on different bioavailability and/or bio-transformation of the bioactive compounds, on hormetic phenomenon and/or induced adaptation, or on the synergistic/additive effects of these compounds.

Experiment 2

The second experiment consisted of the measuring of the concentration of peroxides in the serum of mice treated with AOM compared to untreated controls and the verification of the protective effect of the Db0%.

The concentration of peroxides (measured as equivalents of $H_2O_2$) is a parameter that is an index of the oxidative stress of the individual.

Figure 4:
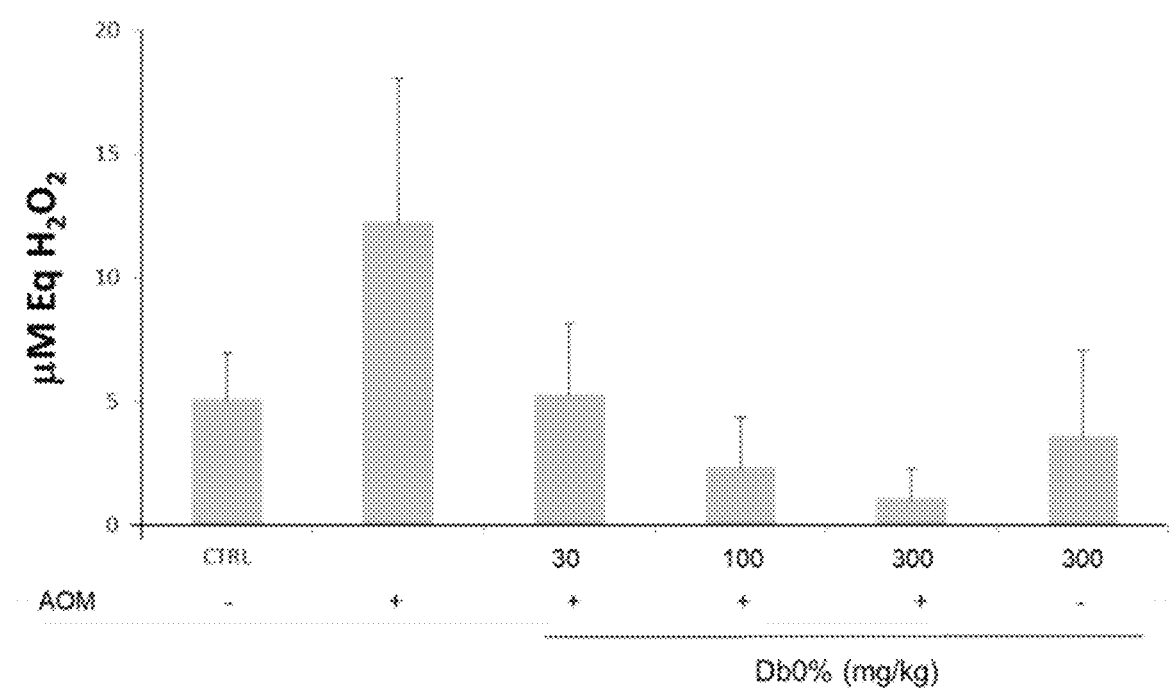
FIG. 4 shows an assay with peroxides (expressed as equivalents of hydrogen peroxide) in samples of serum of mice treated with the concentrations indicated of polyphenolic composition provided by this invention in the presence/absence of AOM.
Figure 5:
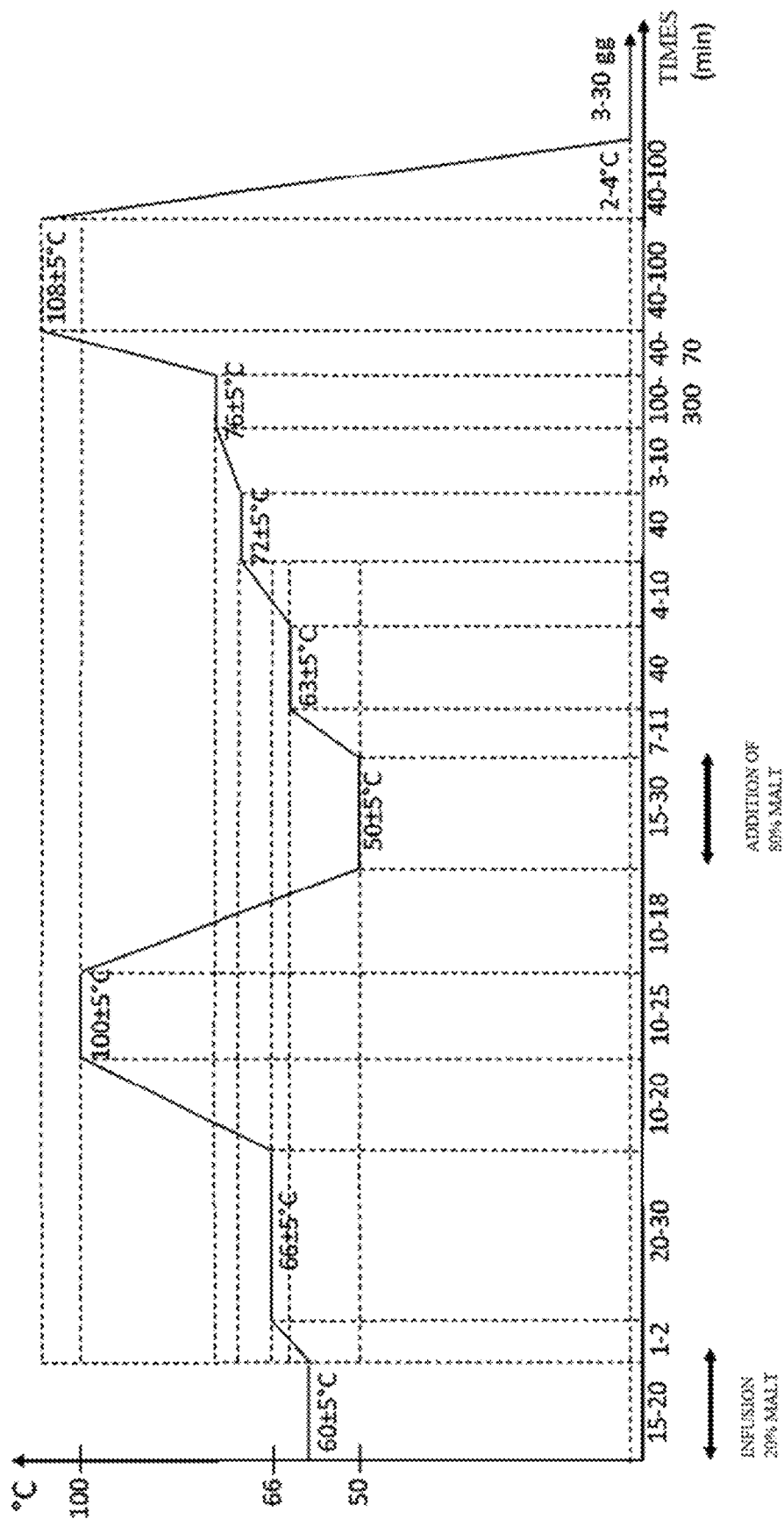
FIG. 5 is a graph of the exemplary thermal cycle of the production method of the polyphenolic composition that this invention provides.

FIG. 4 highlights the concentration of peroxides in samples of serum from treated mice with different concentrations of dried Db0% (3-30-100-300 mg/kg) both in the presence and absence of AOM.

FIG. 4 illustrates how the treatment with AOM to which the mice were subjected, causes a significant increase in the concentration of the peroxides in the serum; the treatment with Db0% causes a reduction in the concentration of peroxides in the serum of mice and, in particular, at higher concentrations of 100-300 mg/kg, the concentration of peroxides become less than the control value.

Even in the last column, the administering of Db0% at a concentration of 300 mg/kg in animals not treated with AOM caused a reduction in the concentration of peroxides in the serum, confirming the anti-oxidant power of the Db0% preparation.

The advantages of this invention are represented by having perfected an innovative method that preserves the polyphenolic content in barley malt naturally, without having to add polyphenols, beginning with raw materials that are easy to find. One of the advantages of this invention is represented by the doses necessary to achieve a potentially therapeutic action; indeed, in the experiments reported, it is the lowest dosage, or 3 mg/kg, that causes the most important therapeutic activity in both preneoplastic lesions and tumoral lesions; in making a correspondence and calculating the quantity in ml that a man of an average weight of 70 kg should take to obtain the anti-tumor effect observed with concentrations of 3-30 mg/kg, extremely low values of about 2-20 ml were obtained. As a result of the above, this invention describes a method for the production of a polyphenolic composition from unfermented malt and hops, wherein the illustrated embodiments provide a composition with a high content of natural polyphenols and an anti-oxidant and anti-tumor action in experimental models at doses 100 times lower than toxic ones.

The object of the invention is susceptible to numerous modifications and variants, all under the same inventive concept disclosed in the attached claims.

All parts may be replaced with other technically equivalent elements, and the materials may differ according to needs, without departing from the scope of protection of the present invention.

Although the object was described with particular reference to the attached figures, the reference numbers used in the description and in the claims are used for a better understanding of the invention and do not constitute any limitation to the disclosed scope of protection.

BIBLIOGRAPHY CITED

Benitez J R, Forster A, De Keukeleire D, Moir M, Sharpe R, Verhagen L C, Westwood K T (1997) Hops and Hop Products. Nürnberg, Germany Gerhauser C (2005) BEER constituents as potential cancer chemopreventive agents. Eur J Cancer 41(13): 1941-54

Ghiselli A, Natella F, Guidi A, Montanari L, Fantozzi P, Scaccini C (2000) BEER increases plasma antioxidant capacity in humans. J Nutr Biochem 11(2): 76-80

Kondo K (2004) BEER and Health: preventive effects of BEER components on lifestyle-related diseases. Biofactors 22(1-4): 303-10

Lust S, Vanhoecke B, Janssens A, Philippe J, Bracke M, Offner F (2005) Xanthohumol kills B-chronic lymphocytic leukemia cells by an apoptotic mechanism. MolNutr Food Res 49(9): 844-50

Miranda C L, Stevens J F, Helmrich A, Henderson M C, Rodriguez R J, Yang Y H, Deinzer M L, Barnes D W, Buhler D R (1999) Antiproliferative and cytotoxic effects of prenylated flavonoids from hops (*Humulus lupulus*) in human cancer cell lines. Food ChemToxicol 37(4): 271-85

Nelson R L, Samelson S L. (1985) Neither dietary ethanol nor beer augments experimental colon carcinogenesis in rats. Dis Colon Rectum 28(6):460-2.

Rivero D, Perez-Magarino S, Gonzalez-Sanjose M L, Valls-Belles V, Codoner P, Muniz P (2005) Inhibition of induced DNA oxidative damage by BEERs: correlation with the content of polyphenols and melanoidins. J Agric Food Chem 53(9): 3637-42

Tedesco I, Nappo A, Petitto F, Iacomino G, Nazzaro F, Palumbo R, Russo G L (2005) Antioxidant and cytotoxic properties of lyophilized BEER extracts on HL-60 cell line. Nutr Cancer 52(1): 74-83

Francesco Visioli, Catalina Alarcón De La Lastra, Cristina Andres-Lacueva, Michael Aviram, Coneição Calhau, Alfredo Cassano, Massimo D'Archivio, Ana Faria, Gaëlle Favé, Vincenzo Fogliano, Rafael Llorach, Paola Vitaglione, Mario Zoratti & Marvin Edeas (2011) Polyphenols and Human Health: A Prospectus, Critical Reviews in Food Science and Nutrition, 51:6, 524-546

Daniele Del Rio, Ana Rodriguez-Mateos, Jeremy P. E. Spencer, Massimiliano Tognolini, Gina Borges, and Alan Crozier. Dietary (Poly)phenolics in Human Health: Structures, Bioavailability, and Evidence of Protective Effects Against Chronic Diseases. Antioxid. Redox Signal. 18, 1818-1892, 2013.

The invention claimed is:

1. A method for producing a polyphenolic composition, the method comprising:
   1) grinding malt grains and splitting in two portions;
   2) mixing each of the two portions with water to obtain a mixture A and a mixture B, wherein mixture A has a malt concentration from 9.5% to 20% by weight and mixture B has a malt concentration from 33% to 60% by weight;

3) thermal cycling in a first phase mixture A until the mixture boils;

4) following thermal cycling of mixture A, combining mixture A and mixture B;

5) thermal cycling in a second phase the combination of mixture A and mixture B wherein the thermal cycling in the second phase comprises staged heating with temperature increasing between 60° C. and 80° C.;

6) separating from the combination of mixture A and mixture B a liquid component and a solid component comprising spent grains;

7) adding hops to the liquid component to obtain a beer wort;

8) boiling the beer wort; and 9) cooling the beer wort until a temperature between 2° C. and 10° C. is reached to obtain the polyphenolic composition;

wherein the second phase of the thermal cycling comprises holding temperature between 45° C. and 55° C. for 15-30 minutes, followed by a subsequent three stage heating with increasing temperatures between 60° C. and 80° C., and wherein the three stage heating with increasing temperatures is conducted as follows:

the first heating stage at 63±5° C. is reached in 7-11 minutes and hold for about 37-42 minutes;

the second heating stage at 72±5° C. is reached in 4-10 minutes and hold for about 37-42 minutes; and the third heating stage at 76±5° C. is reached in 3-10 minutes and hold for about 100-300 minutes.

2. The method of claim 1, further comprising aging the beer wort for at least 3 days.

3. The method of claim 2, further comprising at least one of the following steps:

purifying the beer wort to remove impurities;

adding a natural preservative to the beer wort; or pasteurizing the beer wort.

4. The method of claim 1, further comprising washing the solid component comprising spent grains with water and mixing the wash obtained therefrom with the liquid component.

5. The method of claim 1, wherein separating from the combination of mixture A and mixture B the liquid component and the solid component comprising spent grains is performed at the final temperature reached in the second phase thermal cycling.

6. The method of claim 1, wherein yeast is not added during the process.

7. The method of claim 1, wherein mixture A contains 20% by weight of the malt grains and mixture B contains 80% by weight of the malt grains.

8. The method of claim 1, wherein the first phase of the thermal cycling comprises heating for a period of 1-2 minutes until reaching a temperature of 66±5° C.; a following pause holding the temperature for 20-30 minutes, followed by a raise in temperature for a duration of 10-20 minutes until the mixture is boiled; a following boiling pause for 10-25 minutes, followed by cooling for a duration of 10-18 minutes to a temperature between 45° C. and 55° C.

9. The method according to claim 1, wherein beer wort contains up to 0.5% by weight of hops.

10. The method according to claim 1, wherein the boiling the beer wort comprises heating to the boiling point at 108° C. for about 60 minutes.

11. The method of claim 1, wherein the first phase of the thermal cycling comprises heating for a period of 1-2 minutes until reaching a temperature of approximately 66° C.; a following pause holding the temperature for approximately 20 minutes followed by a raise in temperature for a duration of approximately 15-16 minutes until the mixture is boiled; a following boiling pause for 10-25 minutes, followed by cooling for a duration of approximately 14 minutes to a temperature between 45° C. and 55° C.

* * * * *